(12) United States Patent
Kiritsis

(10) Patent No.: US 8,523,861 B2
(45) Date of Patent: Sep. 3, 2013

(54) METHOD AND APPARATUS FOR OSTEOSYNTHESIS

(75) Inventor: Paul Kiritsis, Midlothian, VA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 286 days.

(21) Appl. No.: 12/871,423

(22) Filed: Aug. 30, 2010

(65) Prior Publication Data

US 2012/0053586 A1 Mar. 1, 2012

(51) Int. Cl.
*A61B 17/58* (2006.01)

(52) U.S. Cl.
USPC ............................ 606/71; 606/96; 606/280

(58) Field of Classification Search
USPC ................. 606/96, 97, 70, 71, 282–289, 246, 606/295, 296
See application file for complete search history.

(56) References Cited

U.S. PATENT DOCUMENTS

| | | | | |
|---|---|---|---|---|
| 4,794,918 A | * | 1/1989 | Wolter | 606/295 |
| 4,988,350 A | | 1/1991 | Herzberg | |
| 5,006,120 A | | 4/1991 | Carter | |
| 5,484,439 A | | 1/1996 | Olson et al. | |
| 6,059,789 A | * | 5/2000 | Dinger et al. | 606/96 |
| 6,224,602 B1 | * | 5/2001 | Hayes | 606/296 |
| 6,402,756 B1 | | 6/2002 | Ralph et al. | |
| 7,591,840 B2 | | 9/2009 | Suddaby | |
| 7,758,616 B2 | * | 7/2010 | LeHuec et al. | 606/246 |
| 2004/0068319 A1 | * | 4/2004 | Cordaro | 623/17.11 |
| 2005/0015093 A1 | * | 1/2005 | Suh et al. | 606/96 |
| 2005/0085818 A1 | * | 4/2005 | Huebner | 606/69 |
| 2005/0149026 A1 | * | 7/2005 | Butler et al. | 606/69 |
| 2006/0264947 A1 | | 11/2006 | Orbay et al. | |
| 2007/0162013 A1 | * | 7/2007 | Jacene et al. | 606/69 |
| 2007/0270853 A1 | | 11/2007 | Leung | |
| 2009/0234359 A1 | | 9/2009 | Onoue et al. | |
| 2011/0218533 A1 | * | 9/2011 | Prandi et al. | 606/71 |
| 2012/0095466 A1 | * | 4/2012 | Winslow et al. | 606/71 |

FOREIGN PATENT DOCUMENTS

DE 102005043281 A1 3/2007

OTHER PUBLICATIONS

"3.5 mm LCP® Proximal Humerus Plate, Stainless Steel and Titanium, Technique Guide", Brochure. Copyright 2002 SYNTHES (USA), Rev. Jun. 2004. 12 sheets.

"Locking Compression Plate (LCP™) System. Locking screw technology and conventional plating in one system." Brochure. Copyright 2003 Synthes, Inc. or its affiliates. Jan. 2007. 6 sheets.

(Continued)

*Primary Examiner* — Todd Manahan
*Assistant Examiner* — Jessica Weiss
(74) *Attorney, Agent, or Firm* — Harness, Dickey

(57) ABSTRACT

A proximal humeral plate assembly can include a first plate, a coupler, a second plate, and a guide. The first plate can define a window and can have a first major surface adapted to conform to a native bone structure. The coupler can be formed on a second major surface of the first plate opposite the first major surface. The second plate can be adapted to engage the coupler, to cover the window, and to conform to the native bone structure. The second plate can include through holes adapted to receive bone screws. The guide can be adapted to engage the coupler and to guide at least one of a cutting tool and a dilation tool.

23 Claims, 10 Drawing Sheets

(56) References Cited

OTHER PUBLICATIONS

"PERI-LOC™ Upper Extremity Locked Plating System", Orthopaedic Trauma & Clinical Therapies, Smith & Nephew, Inc., Brochure. Aug. 2006. www.smith-nephew.com, http://www.mediportgrup.com/Upperextremityvlp.pdf, 30 sheets.

"Zimmer® Universal Locking System", Brochure. Copyright 2006, 2008, 2009 Zimmer, Inc. Rev. Jan. 1, 2010. 2 sheets.

Lee, Churl-Woo, Shin, Sang-Jin. Prognostic factors for unstable proximal humeral fractures treated with locking-plate fixation. *J Shoulder Elbow Surg*. Jan./Feb. 2009. vol. 18, Issue 1, pp. 83-88. Copyright 2009 by *Journal of Shoulder and Elbow Surgery* Board of Trustees.

Robinson, C. Michael, PAGE, Richard S. Severely Impacted Valgus Proximal Humeral Fractures. Surgical Technique. *J Bone Joint Surg Am*. Sep. 2004, vol. 86A, Supplement 1, Part 2, pp. 143-155. Copyright 2004 by the Journal of Bone and Joint Surgery, Incorporated.

Russo, Rafaele et al. The block-bridge system: A new concept and surgical technique to reconstruct articular surfaces and tuberosities in complex proximal humeral fractures. *J Shoulder Elbow Surg*. Jan./Feb. 2008. vol. 17, No. 1, pp. 29-36. Copyright 2008 by *Journal of Shoulder and Elbow Surgery* Board of Trustees.

\* cited by examiner

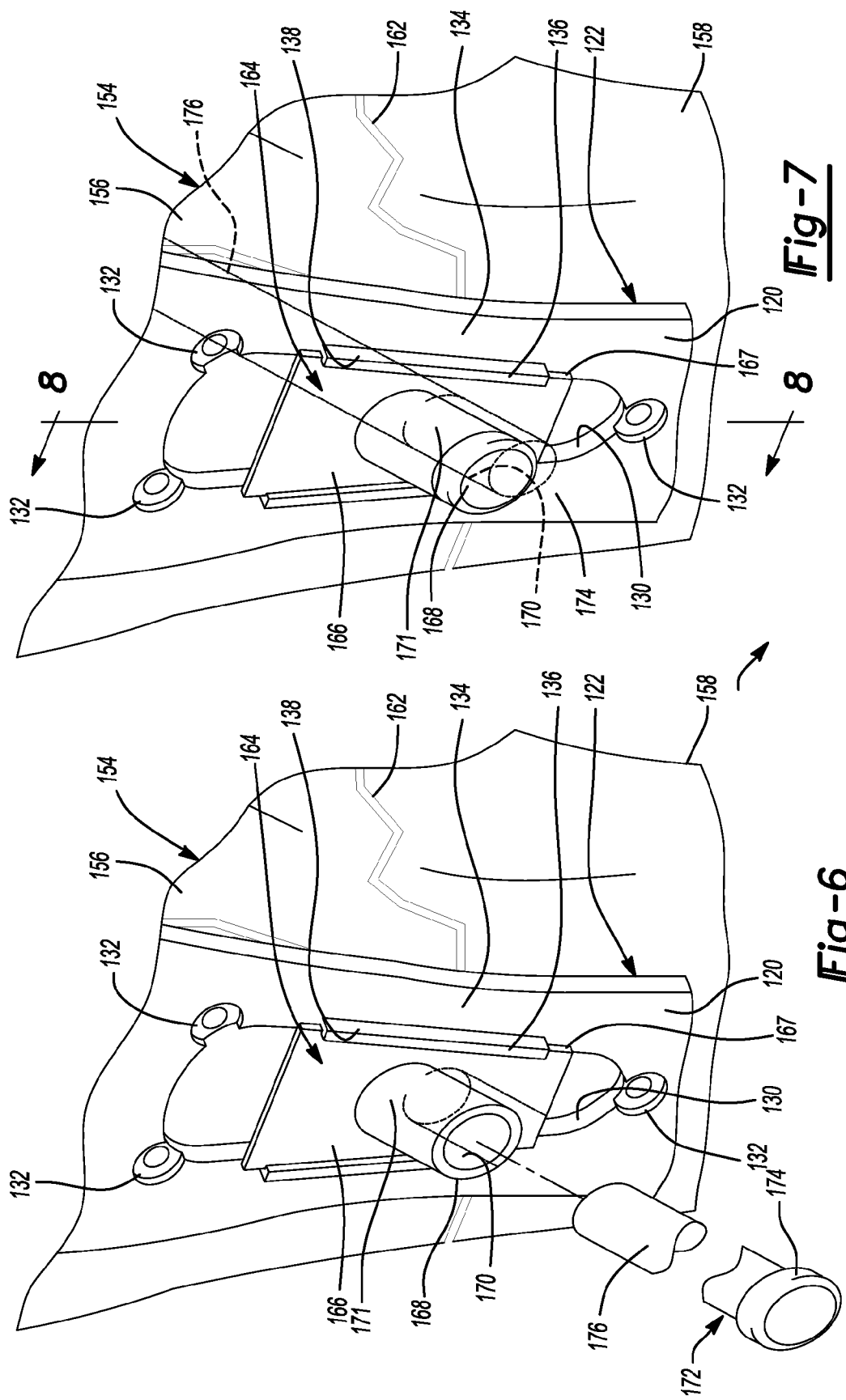

METHOD AND APPARATUS FOR OSTEOSYNTHESIS

FIELD

The following relates to orthopaedic bone plates, and more specifically, relates to plates for reducing and fixing a fractured proximal humerus.

BACKGROUND

The statements in this section merely provide background information related to the present disclosure and does not constitute prior art.

Orhthopaedic bone plates have been developed for osteosynthesis, or the reduction and fixation, of complex fractures in the proximal humerus. Typically, anatomic reduction is performed on fragments of a bone before fixing the fragments to the bone via plates and fasteners. The fragments are then fixed to the bone while the bone heals to improve anatomic alignment of the fragments and minimize anatomic congruities and dysfunction. However, anatomic reduction tends to leave a void adjacent to a realigned or repositioned fragment. Voids that remain after anatomic reduction impede healing, increasing rates of nonunion, malunion, and avascular necrosis.

Thus, there is need for procedures and plating assemblies that facilitate filling voids created by performing anatomic reduction on bone fragments. Filling voids that remain after performing anatomic reduction promotes healing by, for example, restoring vascularity to bone fragments.

SUMMARY

A proximal humeral plate assembly can include a first plate, a coupler, a second plate, and a guide. The first plate can define a window and can have a first major surface adapted to conform to a native bone structure. The coupler can be formed on a second major surface of the first plate opposite the first major surface. The second plate can be adapted to engage the coupler, to cover the window, and to conform to the native bone structure. The second plate can include through holes adapted to receive bone screws. The guide can be adapted to engage the coupler and to guide at least one of a cutting tool and a dilation tool.

A method for osteosynthesis of a fracture in a proximal humerus can include fixing a first plate to the proximal humerus when a fractured portion of the proximal humerus is anatomically aligned and accessible through a window included in the first plate, engaging a guide with a coupler formed on the first plate, removing a lateral cortex of the proximal humerus using a cutting tool inserted through a hole in the guide, and filling the dilated cancellous portion of the proximal humerus by delivering a filler through the hole in the guide.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 6 is a perspective view of the main plate, bone, and guide of FIG. 5 and a dilation tool according to various teachings of the present disclosure;

FIG. 7 is a perspective view of the main plate, bone, and guide of FIG. 5 and the dilation tool of FIG. 6 inserted into the bone and aligned via the guide;

DESCRIPTION OF VARIOUS EMBODIMENTS

Figure 1:
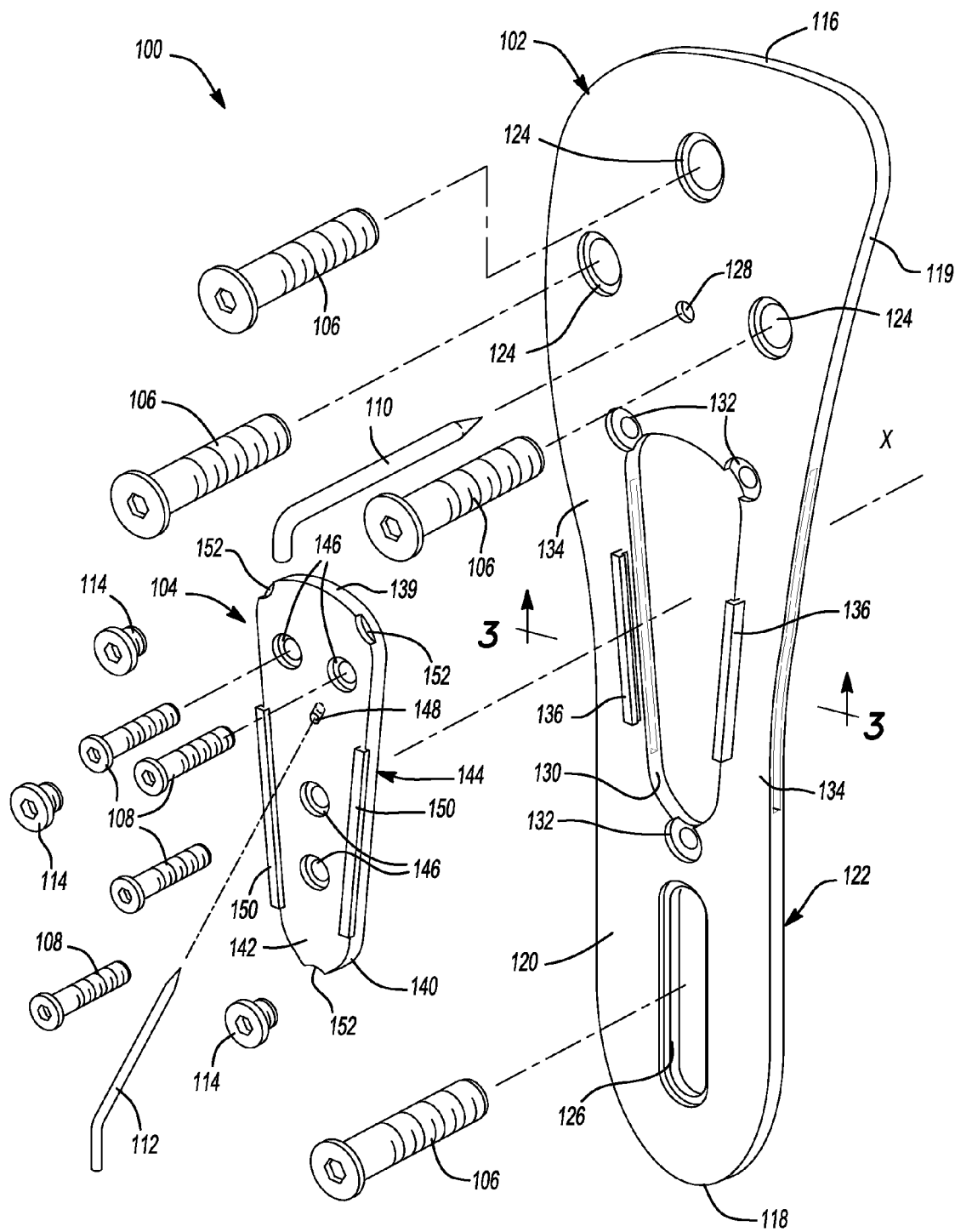
FIG. 1 is an exploded isometric view of a first exemplary bone plate assembly according to various teachings of the present disclosure.

The following description is merely exemplary in nature and is not intended to limit the present disclosure, application, or uses. It should be understood that throughout the drawings, corresponding reference numerals indicate like or corresponding parts and features.

Figure 2:
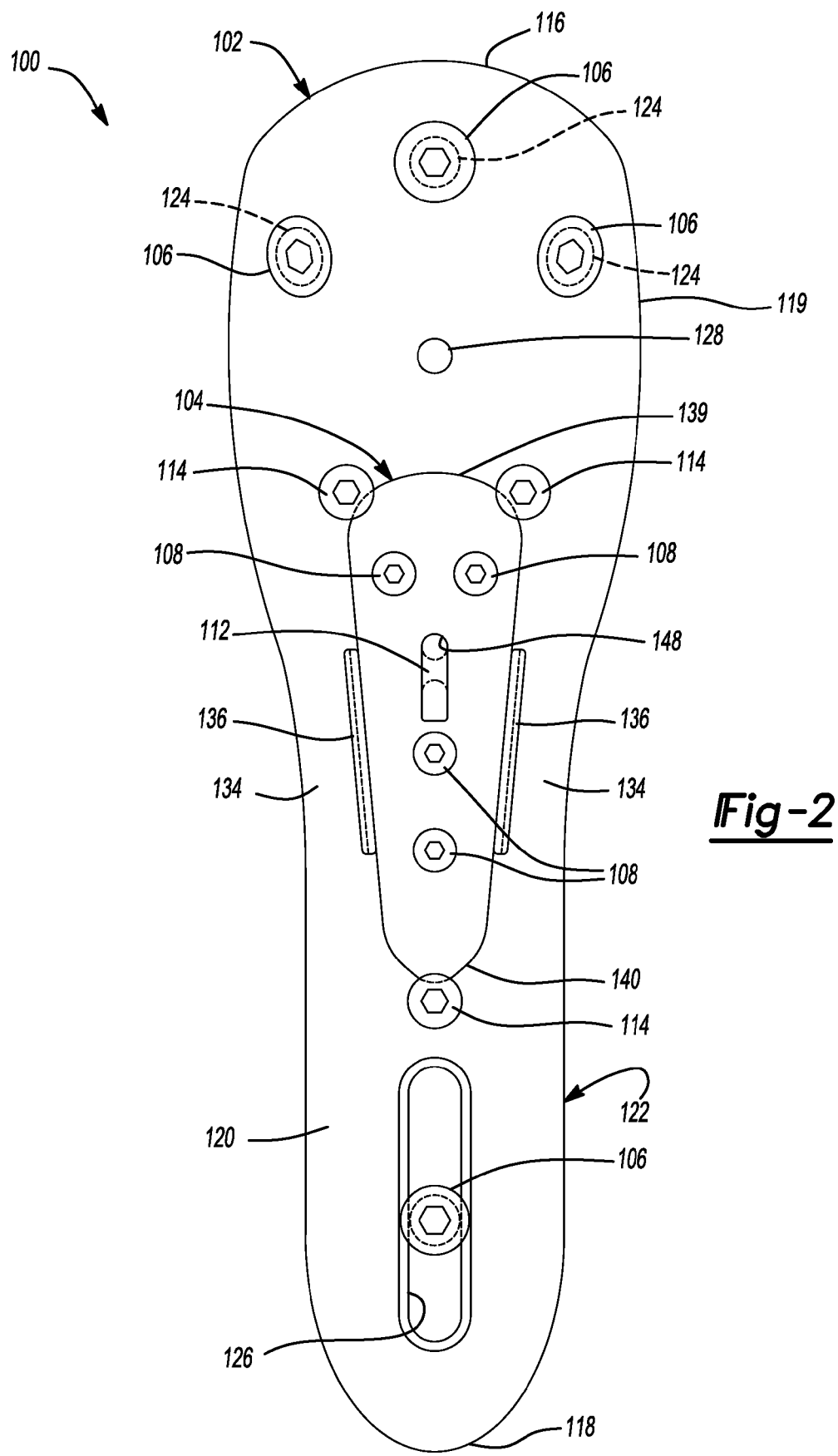
FIG. 2 is a plan view of the bone plate assembly of FIG. 1.
Figure 3:
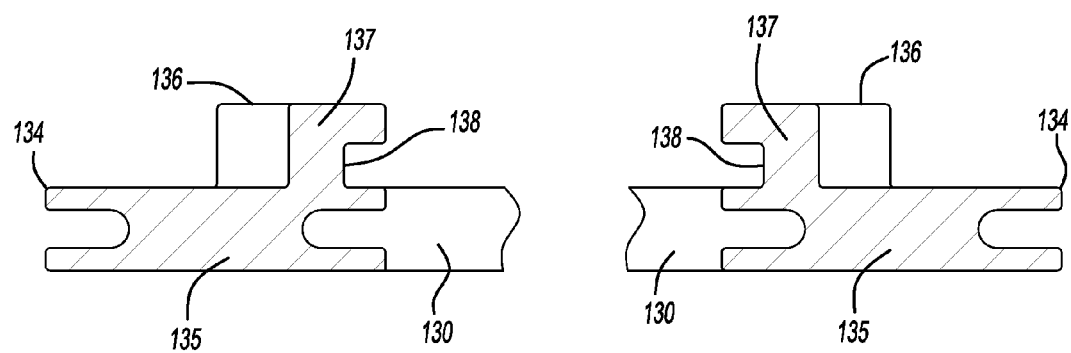
FIG. 3 is a sectional view of a main plate included in the bone plate assembly taken along the line 3-3 of FIG. 1.

Referring to FIGS. 1 through 3, a bone plate assembly 100 is illustrated according to various exemplary embodiments of the present disclosure. The bone plate assembly 100 can include a first or main plate 102, a second or cover plate 104, main plate bone screws 106, cover plate bone screws 108, an main plate Kirchner wire (K wire) 110, an cover plate K wire 112, and set screws 114. The main and cover plates 102, 104 can be shaped to substantially or generally conform to or mate with a plate-engaging surface of a bone, such as a lateral surface of a proximal humerus.

The bone screws 106, 108 can be inserted into the main and cover plates 102, 104, respectively, to attach the main and cover plates 102, 104 to a bone. The K wires 110, 112 can be inserted into the main and cover plates 102, 104, respectively, to hold bone fragments together and to position the bone fragments. Set screws 114 can be used to fasten the cover plate 104 to the main plate 102 when the main plate 102 is fixed to a bone.

The main plate 102 can include a first end 116, a second end 118, an outer edge 119, a first or screw-receiving surface 120 opposite a second or bone-engaging surface 122, screw holes 124, a slot 126, a pin hole 128, an opening or window 130, and partial holes 132. The main plate 102 can be sized to generally cover a plate-engaging surface of a bone without extending beyond the plate-engaging surface. In this regard, the first end 116 can have a greater width than the second end 118 such that the first end 116 generally covers the head of a bone while the second end 118 generally covers the neck of the bone.

The width of the first end 116 can be greater than the width of the second end 118 and the outer edge 119 can be rounded to prevent scarring of soft tissue. In various embodiments, the main plate 102 can have a uniform thickness and a side profile of the main plate 102 can be shaped to conform to a plate-engaging surface of a bone. Alternatively, the main plate 102 can have a varying thickness, the second surface 122 can be shaped to conform to a plate-engaging surface of a bone, and the first surface 120 can be shaped differently than the second surface 122.

The screw holes 124 receive the screws 106 to fix the main plate 102 to a bone. The screw holes 124 can be positioned adjacent to the first end 116 of the main plate 102, as shown, or can be positioned elsewhere in the main plate 102. Although three screw holes are shown, the main plate 102 can include more or less screw holes. The screw holes 124 can be threadless counterbores, as shown. Alternatively, the screw holes 124 can be threaded and can be straight or countersunk.

The slot 126 receives one or more of the screws 106 to fix the main plate 102 to a bone. The slot 126 can be positioned adjacent to the second end 118 of the main plate 102, as shown, or can be positioned elsewhere in the main plate 102. The slot 126 can extend substantially along a longitudinal axis x of the main plate 102. The screw 106 can be inserted into the slot 126 first to axially adjust the main plate 102, and then the screws 106 can be inserted into the holes 124 to fix the main plate 102. The slot 126 can be a threadless couterbore, as shown.

The pin hole 128 receives the K wire 110 that holds bone fragments together. The pin hole 128 can be positioned adjacent to the first end 116 of the main plate 102, as shown, or can be positioned elsewhere in the main plate 102. Although one pin hole is shown, the main plate 102 can include more or less pin holes. The pin hole 128 can be normal to the first surface 120 of the main plate 102, as shown, or can be angled relative to the normal of the first surface 120. The pin hole 128 can be angled toward the first end 116 of the main plate 102 as the pin hole 128 extends from the first surface 120 to the second surface 122. Angling the pin hole 128 in this way allows the K wire 110 to extend closer to an end of a bone proximate to the first end 116 of the main plate 102.

The window 130 can extend along the longitudinal axis of the main plate 102 and can receive the cover plate 104. The window 130 can include longitudinal sides 133 that extend generally parallel to the outer edge 119 between rounded corners of the main plate 102. To this end, the end width of the window 130 closest to the first end 116 of the main plate 102 can be greater than the end width of the window 130 closest to the second end 118 of the main plate 102.

The partial holes 132 receive the set screws 114 to secure the cover plate 104 to the main plate 102. The partial holes 132 can be positioned at the rounded corners of the window 130, as shown, or can be positioned at other locations adjacent to the window 130. Although three partial holes are shown, the main plate 102 can include more or less partial holes. The partial holes 132 can include at least part of a counterbore and a threaded bore, as shown. Alternatively, the partial holes 132 can include at least part of a countersink and a threaded bore.

With particular reference to FIG. 3, the main plate 102 can also include ribs 134 having I-shaped cross sections 135, and a coupler or slide mechanism 136 having two L-shaped cross sections 137. The ribs 134 are on either side of the window 130 and extend between the longitudinal sides 133 of the window 130 and the outer edge 119 of the main plate 102. The I-shaped cross section 135 increases the strength of the main plate 102 along the length of the window 130, offsetting strength reduction in this region due to a reduced cross-sectional area. The ribs 134 and the slide mechanism 136 can have rounded corners to prevent soft tissue damage.

The slide mechanism 136 can be formed on the first surface 120 of the main plate 102 such that the L-shaped cross section 137 extends outward from the first surface 120 and laterally toward the longitudinal axis x of the main plate 102. The slide mechanisms 136 and the first surface 120 can define longitudinal channels 138 that extend substantially parallel to the longitudinal sides 133 of the window 130. Alternatively, the slide mechanism 136 and the longitudinal channels 138 can be substantially parallel with the longitudinal axis x of the main plate 102.

The cover plate 104 can include a first end 139, a second end 140, a first surface 142 opposite a second or bone-engaging surface 144, screw holes 146, a pin hole 148, slide rails 150, and partial counterbores 152. The cover plate 104 can be sized to fit within the window 130 in the main plate 102. In this regard, the outer perimeter of the cover plate 104 can conform to or mate with the inner perimeter of the window 130 in the main plate 102. In addition, the cover plate 104 can generally cover the window 130 in the main plate 102 when the cover plate 104 is placed within the window 130. The cover plate 104 can have a uniform or varying thickness matching the thickness of the main plate 102.

The first and second ends 139, 140 of the cover plate 104 can be rounded to conform to the rounded corners of the window 130 in the main plate 102. The first and second surfaces 142, 144 of the cover plate 104 can have a contour that matches the contour of the first and second surfaces 120, 122 of the main plate 102. To this end, the first and second surfaces 142, 144 of the cover plate 104 can provide a gradual transition between portions of the first and second surfaces 120, 122 of the main plate 102 on opposite sides of the window 130 in the main plate 102. As with the second surface 122 of the main plate 102, the second surface 144 of the cover plate 104 can be shaped to conform to a plate-engaging surface of a bone. In addition, the main and cover plates 102, 104 can be bendable to conform to a surface of a bone.

The screw holes 146 receive the screws 108 to fix the cover plate 104 to a bone. The screw holes 146 can be positioned at various positions along the length of the cover plate 104, as shown, or can be positioned elsewhere in the cover plate 104. Although four screw holes are shown, the cover plate 104 can include more or less screw holes. The screw holes 146 can be threadless counterbores, as shown. Alternatively, the screw holes 146 can be threaded and can be straight or countersunk.

The pin hole 148 receives the K wire 112 that holds bone fragments together. The pin hole 148 can be positioned adjacent to the first end 139 of the cover plate 104, as shown, or can be positioned elsewhere in the cover plate 104. Although one pin hole is shown, the cover plate 104 can include more or less pin holes. The pin hole 148 can be perpendicular to the first surface 142 of the cover plate 104, as shown, or can be angled relative to the normal of the first surface 142. The pin hole 148 can be angled toward the first end 139 of the cover plate 104 as the pin hole 148 extends from the first surface 142 to the second surface 144. The pin holes 128, 148 can be positioned generally in the center of the plates 102, 104 along the longitudinal axis x where multiple bone fragments can reside when the plates 102, 104 are fixed to bone.

The slide rails 150 can be formed on the first surface 142 of the cover plate 104 and can be shaped and sized to engage the longitudinal channels 138 defined by the slide mechanism 136 and the first surface 120 of the main plate 102. In this regard, the slide rails 150 can have rectangular cross-sections and can extend laterally beyond longitudinal sides of the cover plate 104. The distance by which the slide rails 150 extend beyond the longitudinal sides of the cover plate 104 can equal the depth of the longitudinal channels 138. The slide rails 150 can have a length equal to the length of the longitudinal channels 138, and can be positioned to engage the longitudinal channels 138 when the cover plate 104 is placed within the window 130.

The partial counterbores 152 in the cover plate 104 cooperate with partial holes 132 in the main plate 102 to form a complete counterbore and a threaded bore that receive the set screws 114 to secure the cover plate 104 to the main plate 102. The partial counterbores 152 provide a recess for the set screws 114 to fit within while securing the cover plate 104. The position and number of the partial counterbores 152 can correspond to the position and number of the partial holes 132. The partial counterbores 152 can complete the partial counterbores of the partial holes 132, as shown.

Figure 9:
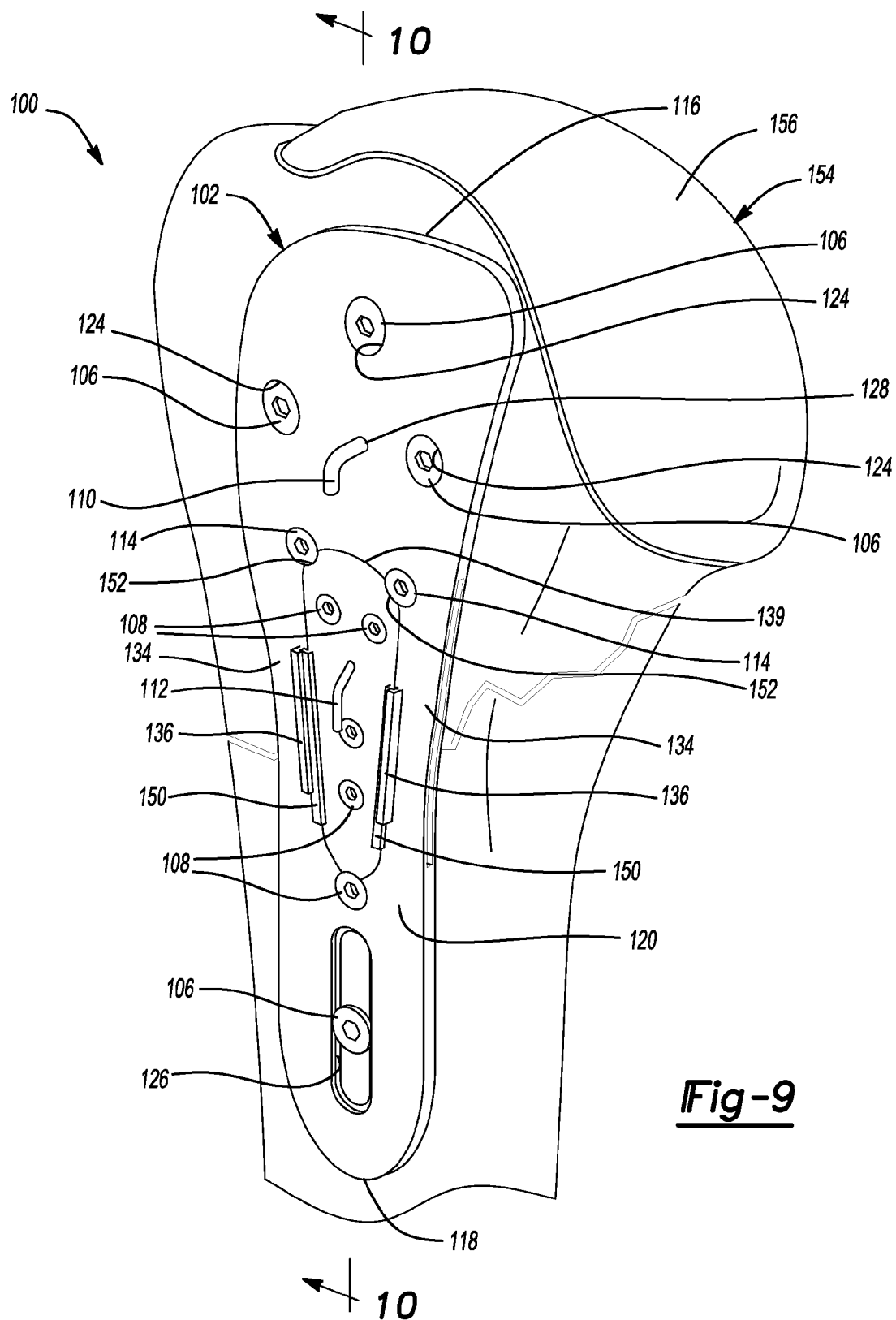
FIG. 9 is a perspective view of the bone plate assembly of FIG. 1 and a reconstructed bone according to various teachings of the present disclosure.
Figure 10:
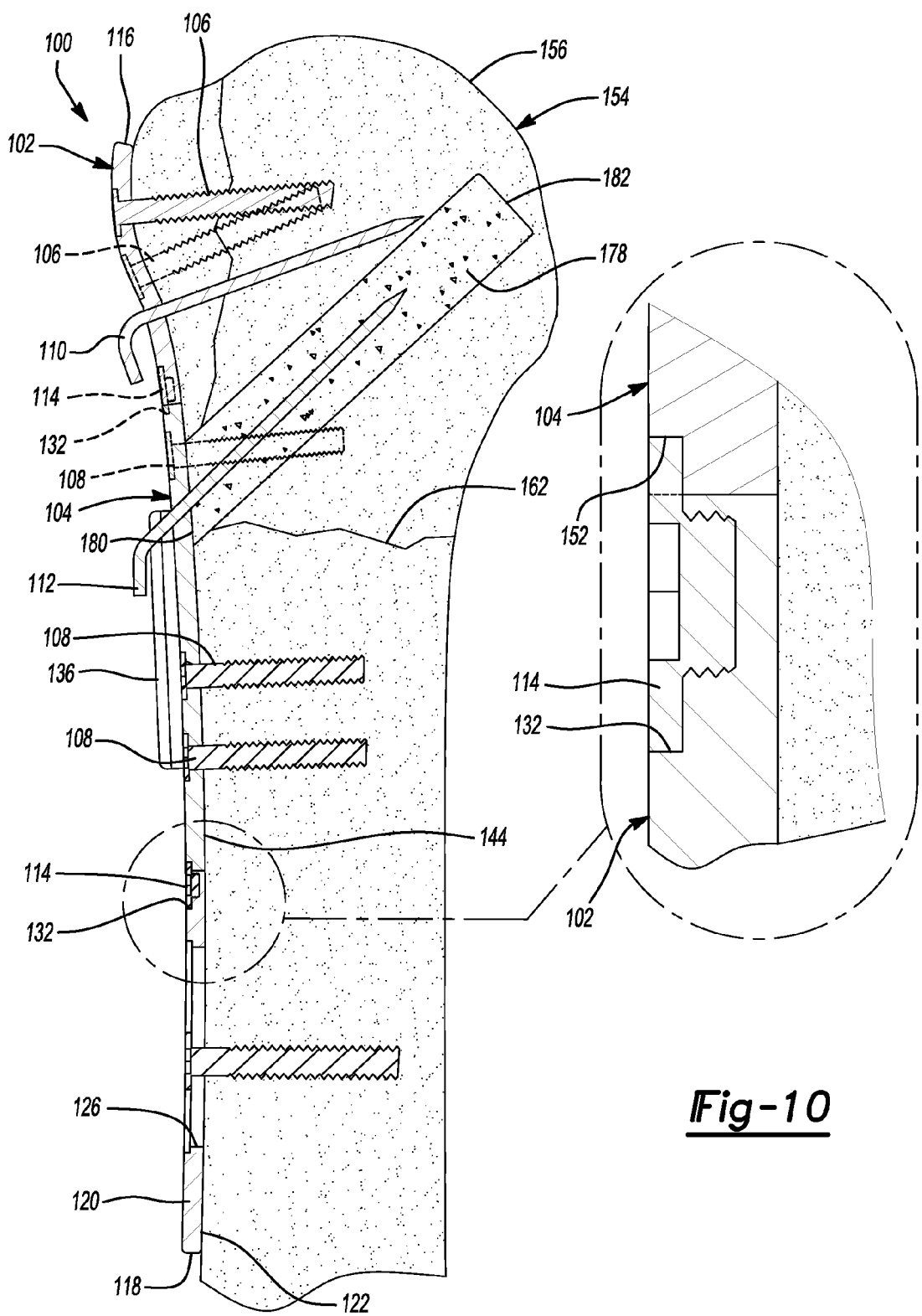
FIG. 10 is a cross-sectional view of the bone plate assembly and reconstructed bone taken alone the line 10-10 of FIG. 9.
Figure 11:
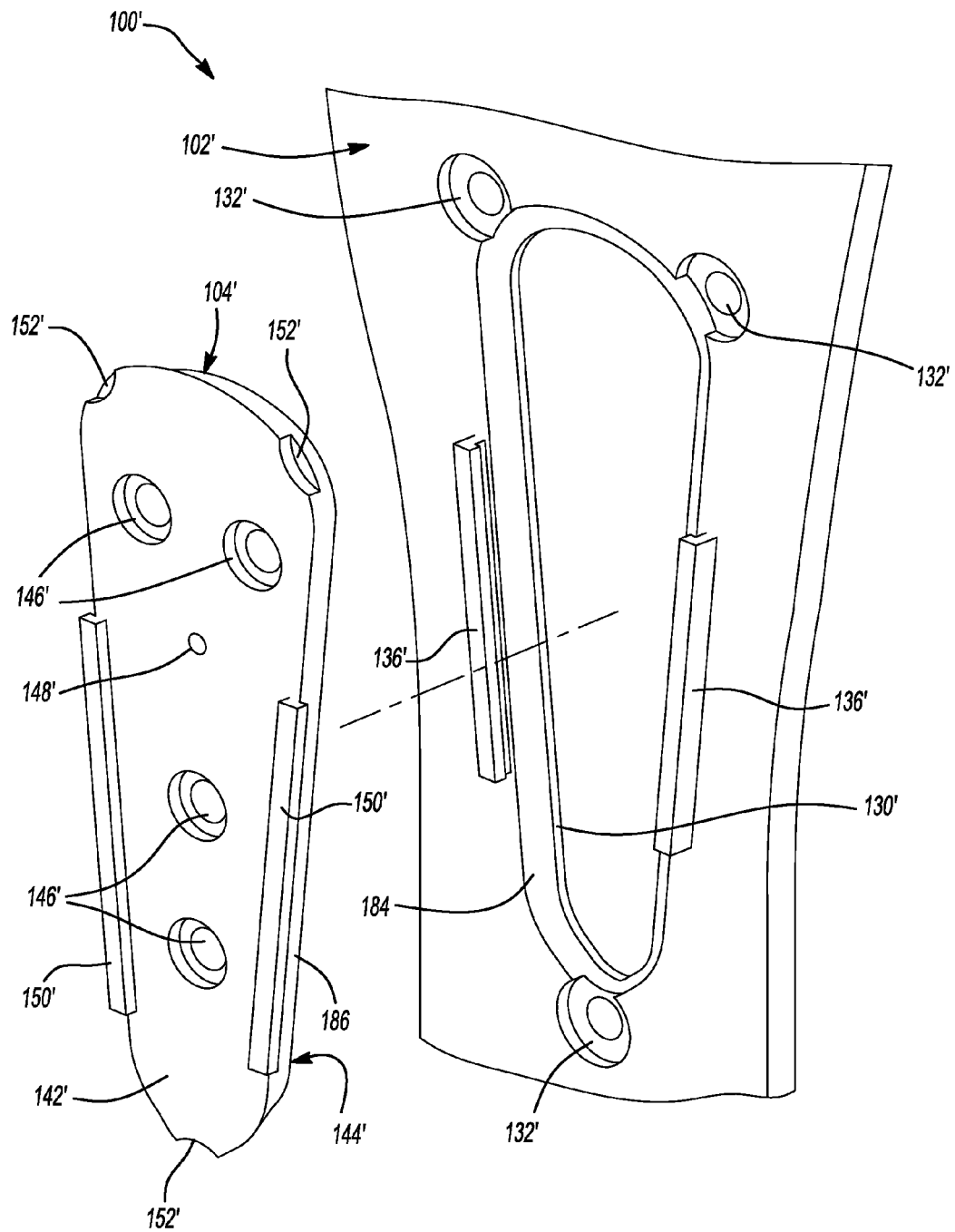
FIG. 11 is an exploded isometric view of a second exemplary bone plate assembly according to various teachings of the present disclosure.

Referring to FIGS. 4 through 11, a method for reduction and fixation of a proximal humerus 154 using a bone plate system according to various exemplary embodiments of the present disclosure will now be described. A bone plate system according to the present disclosure can include various features of the bone plate assemblies 100, a guide 164 (FIGS. 5 through 7), and a bone plate assembly 100' (FIG. 11). The proximal humerus 154 has a head 156, a neck 158, a body 160, and a fracture 162. The fracture 162 can be a two, three, or four part head fracture.

Figure 4:
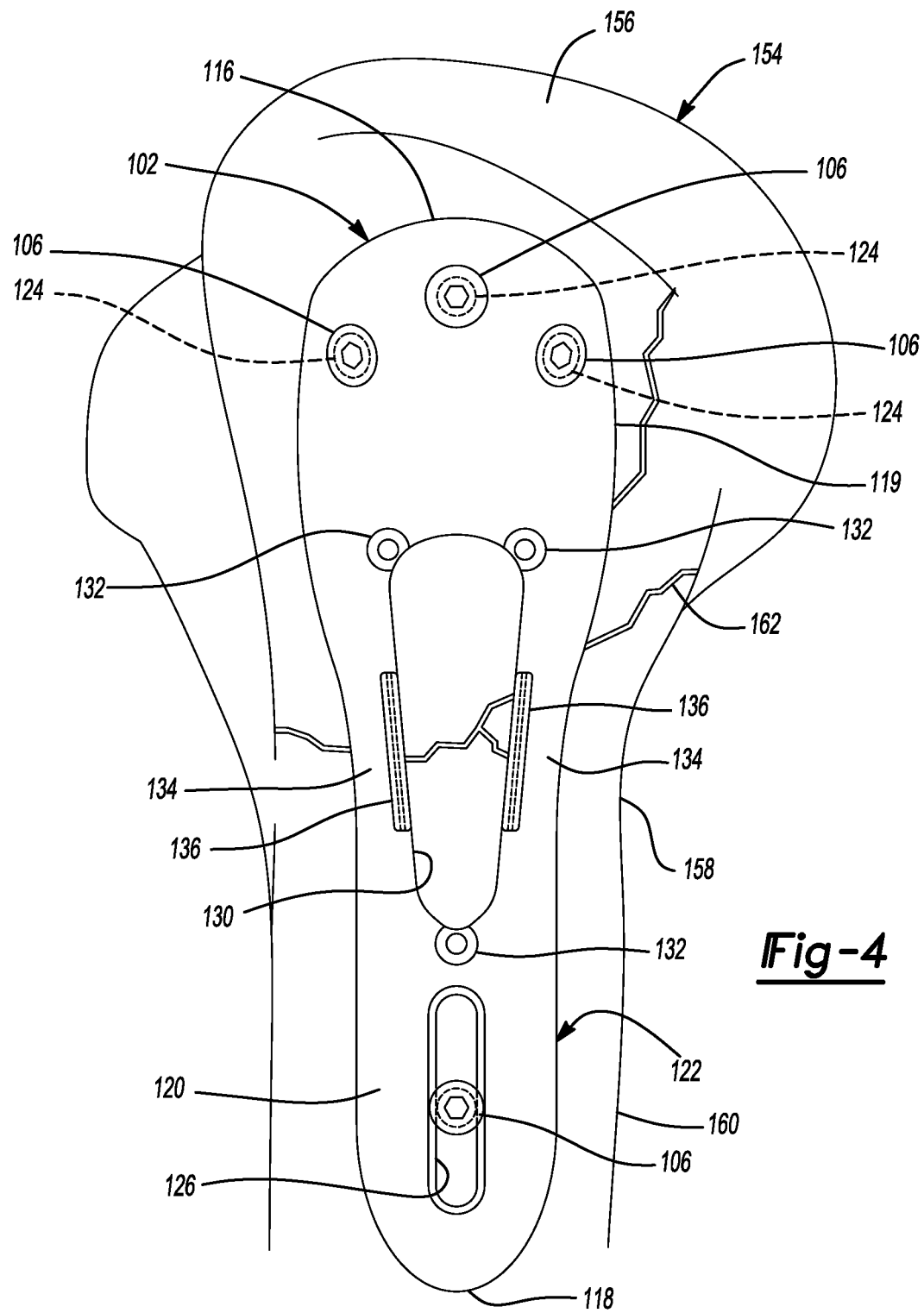
FIG. 4 is a plan view of the main plate of FIG. 3 attached to a bone.

With particular reference to FIG. 4, the main plate 102 can be positioned on the proximal humerus 154 such that the fracture 162 is visible through the window 130 in the main plate 102. The main plate 102 can be positioned such that the window 130 provides access to a fractured portion of the proximal humerus 154 adjacent to the fracture 162. The bone screws 106 can then be inserted through the screw holes 124 and the slot 126 in the main plate 102 and into the proximal humerus 154 to fix the main plate 102 to the proximal humerus 154. Before fixing the main plate 102 to the proximal humerus 154, displaced bone fragments of the head 156 resulting from the fracture 162 can be repositioned or realigned to an anatomically correct position.

Figure 5:
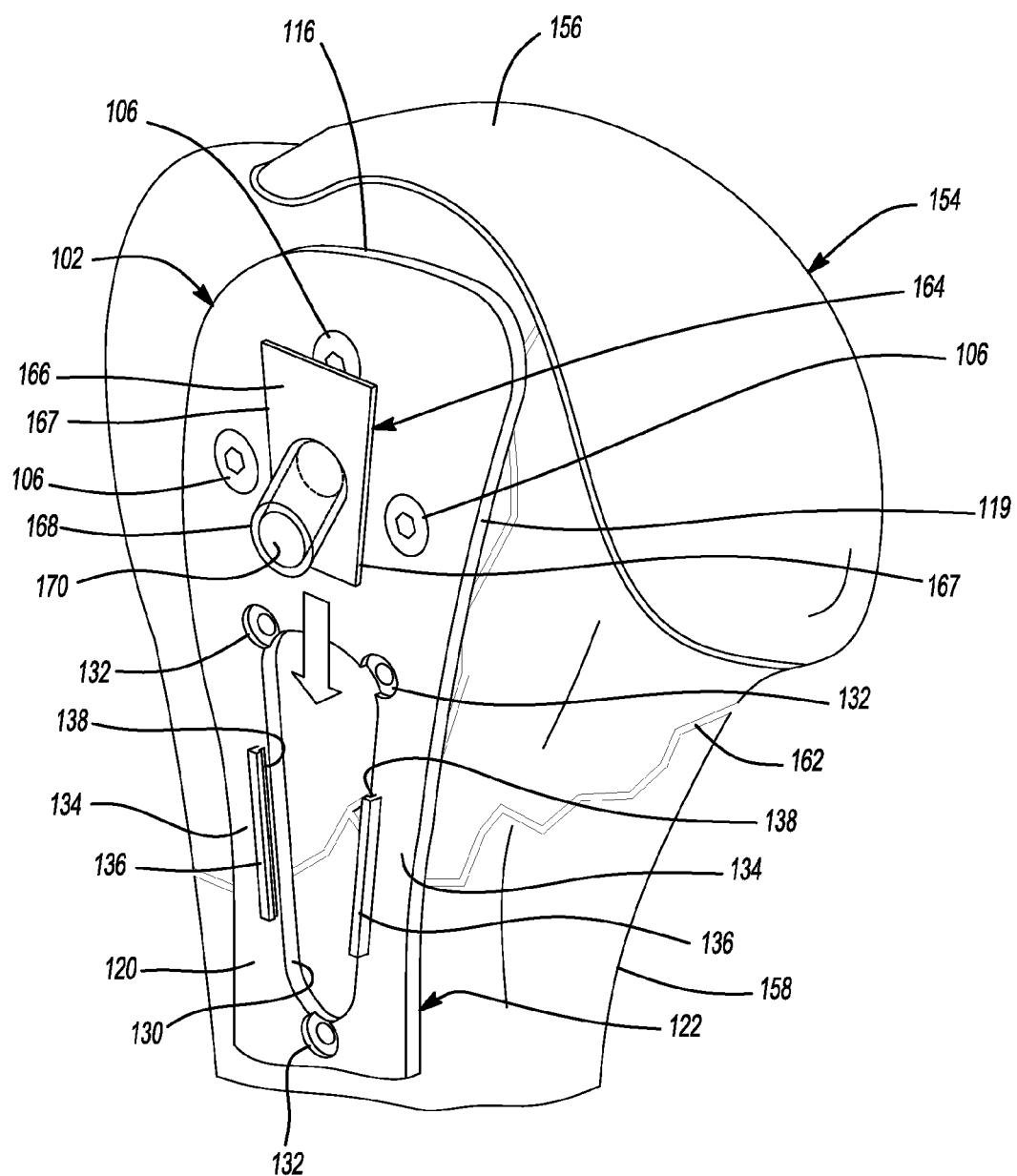
FIG. 5 is a perspective view of the main plate and a bone of FIG. 4 and a guide according to various teachings of the present disclosure.

With particular reference to FIGS. 5 through 7, the guide 164 can include a base 166 having longitudinal edges 167 and a hollow shaft 168 defining a passage 170. The base 166 can be shaped and sized to engage the slide mechanism 136. To this end, the base 166 can be rectangular, and the longitudinal edges 167 can extend laterally outward from one end of the base 166 to another or can be substantially parallel to the longitudinal axis x of the main plate 102. In addition, the thickness of the base can be equal to the height of the longitudinal channels 138.

The hollow shaft 168 can be fixed normal to the base 166 or at a predetermined angle other than ninety degrees relative to the base 166. Alternatively, the hollow shaft 168 can be joined to the base 166 via a rotatable socket such that the angle between the hollow shaft 168 and the base 166 can be adjusted as desired. The passage 170 in the hollow shaft 168 can be sized to receive a cutting tool and/or a dilation tool. The cutting tool can be a burr, a drill, or a saw, and the dilation tool can be a tamp or a punch.

The guide 164 can slidably engage the slide mechanism 136 to position the passage 170 as desired. When the longitudinal channels 138 of the main plate 102 and the longitudinal edges 167 of the guide 164 extend laterally outward in the direction toward the first end 116 of the main plate 102, the narrowing distance between the longitudinal channels 138 can act as a stop when the base 166 of the guide 164 is inserted in the direction away from the first end 116 of the main plate 102, as shown. When the longitudinal channels 138 of the main plate 102 and the longitudinal edges 167 of the guide 164 are parallel, the guide 164 can slide through the length of the slide mechanism 136 without encountering a stop. The passage 170 can be positioned at a desired insertion graft insertion site.

Figure 8:
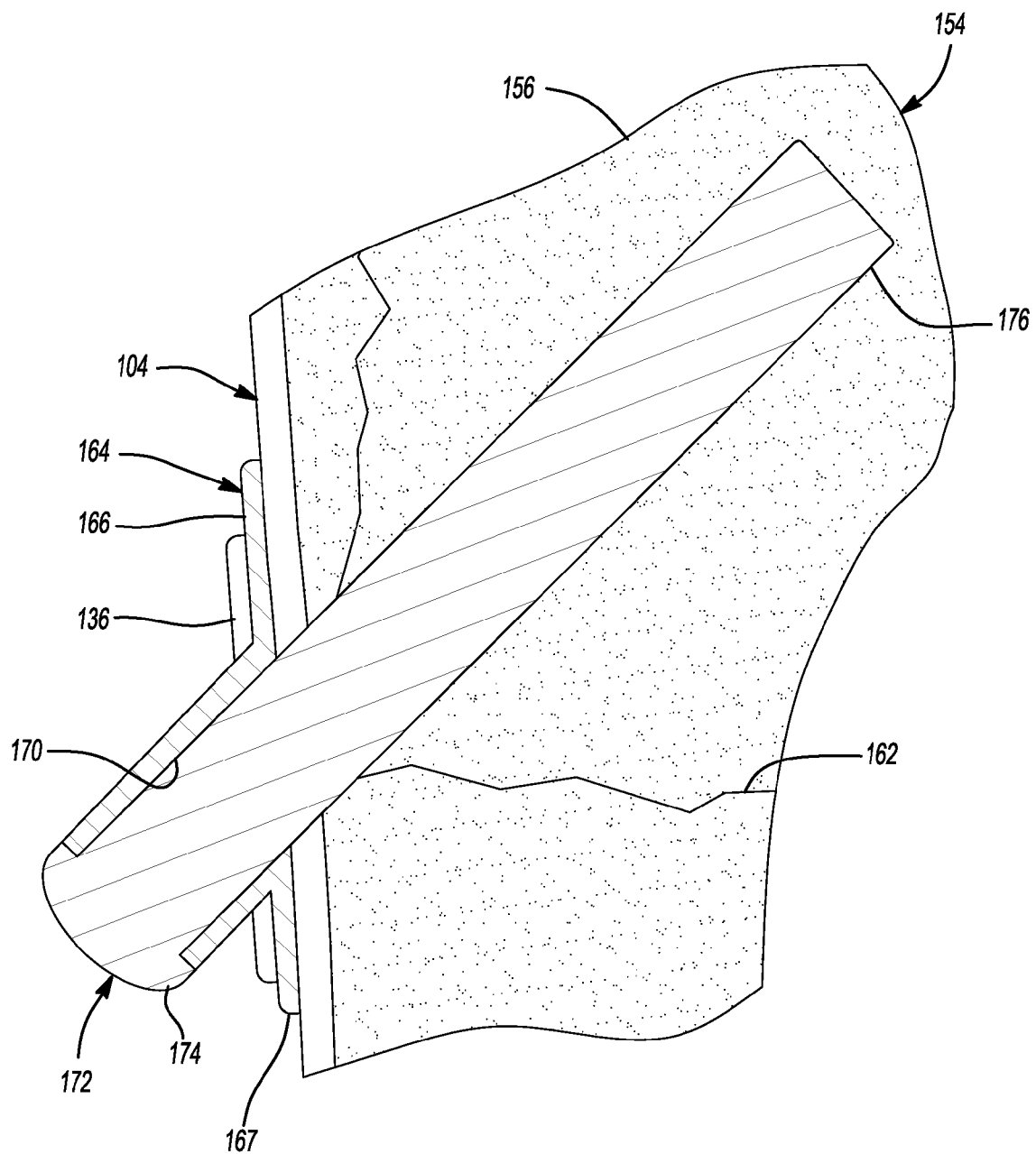
FIG. 8 is a cross-sectional view of the main plate, bone, guide, and dilation tool taken along the line 8-8 of FIG. 7.

With particular reference to FIGS. 6 through 8, when the guide 164 is positioned in a desired position, such as adjacent to a void remaining after realigning fragments of the proximal humerus 154, a tool 172 can be inserted into the guide 164. The tool 172 can include a head 174 and a shaft 176 extending from the head 174. The tool 172 can be a cutting tool, such as a burr or saw, which is operable to remove a lateral cortex 177 of the proximal humerus 154 corresponding to the passage 170 in the guide 164. The lateral cortex 177 can be preserved when removed by, for example, removing the lateral cortex 177 in a single piece.

The tool 172 can also be a dilation tool, such as a tamp or punch, which is operable to dilate or tamp cancellous bone in or near a void remaining after realigning displaced bone fragments of the proximal humerus 154. In this regard, the tool 172 can dilate the void to a known shape and size such that a bone filler 178 can be shaped and sized to fill the void. The bone filler 178 can be shaped and sized based on the portion of the tool 172 extending into the proximal humerus 154 when the head 174 of the tool 172 contacts the hollow shaft 168 of the guide 164.

The tool 172 can be a delivery tool, such as a syringe, that is operable to deliver bone filler into the void. In this regard, the bone filler 178 can be bone graft, bone crush, bone cement, or osteobiologics that can be delivered through the passage 170 of the guide 164 to fill the void in the proximal humerus 154. The bone filler 178 can also be shaped and sized before being delivered to the void based on a measured depth of the dilated void. To this end, the bone filler 178 can be bone graft, such as a fibula allograft, that can generally maintain a shape that fills the void. The tool 172 can tamp solid allograft through the guide 164.

A cutting block can be used to cut the bone filler 178 to the appropriate shape and size to fill the void. In this regard, the cutting block can cut a lateral end 180 of the bone filler 178 at an angle such that the lateral end 180 of the bone filler 178 is generally flush with the lateral surface of the proximal humerus 154 when the bone filler 178 is placed within the void. The angle can be selected based on the angle of the passage 170 relative to the lateral surface of the proximal humerus 154. A medial end 182 of the bone filler 178 can be left uncut (FIG. 10).

With particular reference to FIGS. 9 and 10, when the void has been filled with the bone filler 178, the removed lateral cortex 177 of the proximal humerus 154 can be replaced and the cover plate 104 can be secured within the window 130 of the main plate 102. The slide rails 150 of the cover plate 104 can engage the longitudinal channels 138 as the cover plate 104 is inserted in the direction toward the second end 118 of the main plate 102. When the longitudinal channels 138 and the slide rails 150 extend laterally outward in the direction toward the first end 116 of the main plate 102, the longitudinal channels 138 can act as a stop when the cover plate 104 is slidably inserted in the direction toward the second end 118 of the main plate 102. Alternatively, the longitudinal channels 138 and the slide rails 150 can be substantially parallel with the longitudinal axis x of the main plate 102 and the cover plate 104 can be supported by the main plate 102 within the window 130.

The bone screws 108 can be inserted through the screw holes 146 in the cover plate 104 to secure the cover plate 104 to the proximal humerus 154. The K wires 110, 112 can be inserted through the pin holes 128, 148 before, when, or after the cover plate 104 is secured to the main plate 102. As discussed above, the K wires 110, 112 can be inserted through the pin holes 128, 148 to hold bone fragments together. The pin hole 148 can be aligned with the bone filler 178 when the cover plate 104 covers the window 130 such that the K wire 112 can act as scaffolding for the bone filler when the K wire 112 is inserted in the pin hole 148. The K wires 112, 114 can be used to provisionally fix bone fragments and can be removed when bone screws 106, 108 have been installed to secure the plates 102, 104, respectively, to the proximal humerus 154 and thereby fix the bone fragments.

The set screws 114 can be used to secure the cover plate 104 to the main plate 102. The set screws 114 are inserted into the partial holes 132 of the main plate 102 and into the partial counterbores 152 of the cover plate 104. As best shown in FIG. 10, the heads of the set screws 114 can extend into the partial counterbores 152 of the cover plate 104 to fasten the cover plate 104 without harming soft tissue.

With particular reference to FIG. 11, the bone plate assembly 100' can include a first or main plate 102' having a beveled edge 184 and a second or cover plate 104' having a beveled edge 186. The beveled edge 184 of the main plate 102' can engage the beveled edge 186 of the cover plate 104 to secure the cover plate 104' in all directions except for in the lateral direction away from the proximal humerus 154. In this regard, the set screws 114 can be inserted into partial holes 132' in the main plate 102' and into partial counterbores 152' in the cover plate 104' to secure the cover plate 104' to the main plate 102' in the lateral direction. The bone plate assemblies 100, 100' can include any combination of the slide mechanism 136, the set screws 114, and the beveled edge 184 to secure the cover plates 104, 104' to the main plates 102, 102'.

The foregoing discussion discloses and describes merely exemplary embodiments of the present disclosure. One skilled in the art will readily recognize from such discussion, and from the accompanying drawings and claims, that various changes, modifications and variations can be made therein without departing from the spirit and scope of the disclosure as defined in the following claims. For example, the bone plate assembly 100 can include features of the bone plate assembly 100' and the bone plate assembly 100' can include features of the bone plate assembly 100.

What is claimed is:

1. A proximal humeral plate assembly comprising:
   a first plate defining a window, the first plate having a first major surface adapted to conform to a native bone structure;
   a coupler formed on a second major surface of the first plate opposite the first major surface;
   a second plate adapted to engage a mating surface on the coupler and to cover the window, the second plate including through holes adapted to receive bone screws, the second plate further adapted to conform to the native bone structure; and
   a guide adapted to engage the mating surface on the coupler and to guide at least one of a cutting tool and a dilation tool, the engagement between the guide and the mating surface on the coupler securing the guide to the first plate.

2. The bone plate system of claim 1, wherein mating surface on the coupler is adapted to slidingly receive the guide.

3. The bone plate system of claim 1, wherein the guide is adapted to align the at least one of the cutting tool and the dilation tool at a predetermined angle with respect to the first plate upon engagement with the mating surface.

4. The bone plate system of claim 1, wherein the guide includes a hollow shaft sized to receive the at least one of the cutting tool and the dilation tool.

5. The bone plate system of claim 1, wherein the window is non-circular and has a length extending generally parallel to a longitudinal axis of the first plate.

6. The bone plate system of claim 5, wherein the first plate includes an I-shaped cross-section proximate to longitudinal sides of the window.

7. The bone plate system of claim 1, wherein the coupler includes an L-shaped cross section.

8. The bone plate system of claim 1, wherein the coupler and the first plate define a longitudinal channel adjacent to the window.

9. The bone plate system of claim 8, wherein the guide includes a base adapted to slidably engage the longitudinal channel.

10. The bone plate system of claim 1, wherein the second plate includes a pin hole oriented to receive a pin at an angle.

11. The bone plate system of claim 1, wherein the first plate includes a first partial hole and the second plate includes a second partial hole, the first partial hole and the second partial hole being adapted to receive a set screw to fix the second plate to the first plate.

12. The bone plate system of claim 1, wherein the first plate includes a first beveled edge and the second plate includes a second beveled edge, the first beveled edge and the second beveled edge being adapted to engage each other to secure the second plate relative to the first plate.

13. The bone plate system of claim 1, wherein the engagement between the guide and the mating surface on the coupler movably secures the guide to the first plate.

14. The bone plate system of claim 1, wherein the second plate is sized to fit within the window.

15. The bone plate system of claim 1, wherein an outer perimeter of the second plate conforms to an inner perimeter of the window.

16. A proximal humeral plate assembly comprising:
   a first plate having a bone-engaging first surface and an opposed second surface, the first plate defining a window extending through the first and second surfaces, the bone-engaging first surface adapted to conform to a proximal humerus;
   a slide mechanism formed on the opposed second surface of the first plate;
   a second plate slidably engaged with a mating surface on the slide mechanism and supported by the first plate within the window, the second plate including through holes adapted to receive bone screws, the second plate further adapted to conform to the proximal humerus; and
   a guide adapted to engage the mating surface on the slide mechanism and to guide at least one of a cutting tool and a dilation tool, the engagement between the guide and the mating surface on the slide mechanism securing the guide to the first plate.

17. The proximal humeral plate assembly of claim 16, wherein the guide is adapted to slidably engage the mating surface on the slide mechanism.

18. The proximal humeral plate assembly of claim 16, wherein the mating surface on the slide mechanism and the second surface of the first plate define a longitudinal channel adjacent to the window.

19. The proximal humeral plate assembly of claim 18, further comprising a rail formed on the second plate and adapted to engage the longitudinal channel.

20. The proximal humeral plate assembly of claim 16, wherein the engagement between the guide and the mating surface on the slide mechanism movably secures the guide to the first plate.

21. The proximal humeral plate assembly of claim 16, wherein the second plate is sized to fit within the window.

22. The proximal humeral plate assembly of claim 16, wherein an outer perimeter of the second plate conforms to an inner perimeter of the window.

23. A proximal humeral plate assembly comprising:
- a first plate having a bone-engaging first surface and an opposed second surface, the first plate defining a window extending through the first and second surfaces, the bone-engaging first surface adapted to conform to a proximal humerus;
- a slide mechanism formed on the opposed second surface of the first plate;
- a second plate configured to slidably engage a mating surface on the slide mechanism, the second plate being sized to fit within the window and having an outer perimeter that conforms to an inner perimeter of the window such that the second plate covers the window when the second plate is placed within the window, the second plate including through holes adapted to receive bone screws, the second plate having a bone-engaging surface adapted to conform to the proximal humerus; and
- a guide adapted to engage the mating surface on the slide mechanism and to guide at least one of a cutting tool and a dilation tool, the engagement between the guide and the mating surface on the slide mechanism securing the guide to the first plate to prevent movement of the guide in a direction perpendicular to the first and second surfaces of the first plate.

* * * * *